United States Patent [19]

Shoesmith et al.

[11] Patent Number: Plant 5,924

[45] Date of Patent: Mar. 31, 1987

[54] CHRYSANTHEMUM PLANT NAMED PARASOL

[75] Inventors: Leonard H. Shoesmith, Surry, England; Peter S. Hesse, Bradenton, Fla.

[73] Assignee: Ball Pan Am Plant Company, Parrish, Fla.

[21] Appl. No.: 488,671

[22] Filed: Apr. 26, 1983

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Chrysanthemum plant named Parasol having flat capitulum form and single capitulum type, spoon tipped pink-purple ray florets, variable length spoons, 130–150 mm. diameter across face of capitulum, tall plant height and semi-upright branching pattern, and the fading of its flowers to almost white under very high temperatures.

1 Drawing Figure

1

The present invention comprises a new and distinct cultivar of *Chrysanthemum morifolium*, Ramat., hereinafter referred to by the cultivar named Parasol.

Parasol is a product of a planned breeding program which had the objective of creating new Chrysanthemum cultivars with single capitulum type, flat capitulum form, spoon tipped pink-purple ray florets, 8½ week flowering response, and the ability to produce commercially acceptable quality in a year round pot mum program. Such traits in combination were not present in previously available commercial cultivars.

Parasol was originated from a hybridization made in a controlled breeding program in Westfield, Woking England in 1977. The male and female parents are unknown at this time. Parasol was discovered and selected as one flowering plant within the progeny of the stated parentage by Leonard H. Shoesmith and Peter S. Hesse in November, 1978 in a controlled environment in West Chicago, Ill.

The first act of asexual reproduction of Parasol was accomplished when vegetative cuttings were taken from the initial selection in February, 1979 in a controlled environment in West Chicago, Ill. by a technician working under formulations established and supervised by Leonard H. Shoesmith and Peter S. Hesse. Horticultural examination of selected units initiated March, 1978, has demonstrated that the combination of characteristics as herein disclosed for Parasol are firmly fixed and are retained through successive generations of asexual reproduction.

Parasol has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Parasol, which in combination distinguish this chrysanthemum as a new and distinct cultivar.

1. Flat capitulum form.
2. Single capitulum type.
3. Spoon tipped pink-purple ray florets, fading slightly with age.

2

4. Spoons variable in length of tube.
5. Yellow green (immature) to yellow (mature) disc floret color.
6. Diameter across face of the capitulum 130–150 mm.
7. Tall pot plant height of 350–390 mm. from edge of pot.
8. Semi-upright branching pattern.
9. Flower fades to almost white under very high temperatures.

The accompanying photographic drawing show typical inflorescence and foliage characteristics of Parasol, with colors being as nearly true as possible with illustrations of this type. The drawing is a black and white photograph, with two flowers illustrating the range of flower color of Parasol at high and low night temperatures.

In the following description color references are made to The Royal Horticultural Society Colour Chart. The color values were determined between 1:30–2:00 P.M. on Feb. 16, 1983 under 500 foot candles of natural light at Parrish, Fla.

Classification:

*Botanical.*—*Chrysanthemum morifolium*, Ramat., cv Parasol.

*Commercial.*—Daisy pot mum.

I. INFLORESCENCE

A. Capitulum:

*Form.*—Flat.

*Type.*—Novelty.

*Diameter across face.*—130–150 mm.

B. Corolla of ray florets:

*Color (general tonality from a distance of three meters).*—Magenta.

*Color.*—Tubes white, upper surface of spoons when opening at low temperatures (65°–75° night), 77A, lower surface 77C-D; upper surface of spoons when opening at high temperatures (75°–85° night), 76A-B.

C. Corolla of disc florets:

*Color (mature).*—Yellow.

*Color (immature).*—Yellow-green.

D. Reproductive organs:

*Androecium.*—In disc florets only.

*Gynoecium.*—In both disc and ray florets.

II. PLANTS

A. General appearance:

*Height.*—350–390 mm. from edge of pot.

B. Foliage:

*Color (abaxial).*—147B.

*Color (adaxial).*—147A.

*Shape.*—Deeply lobed and slightly serrated.

We claim:

1. A new and distinct cultivar of Chrysanthemum plant named Parasol, as described and illustrated, and particularly characterized by its flat capitulum form and single capitulum type, spoon tipped pink-purple ray florets, variable length spoons, 130–150 mm. diameter across face of capitulum, tall plant height and semi-upright branching pattern, and the fading of its flowers to almost white under very high temperatures.

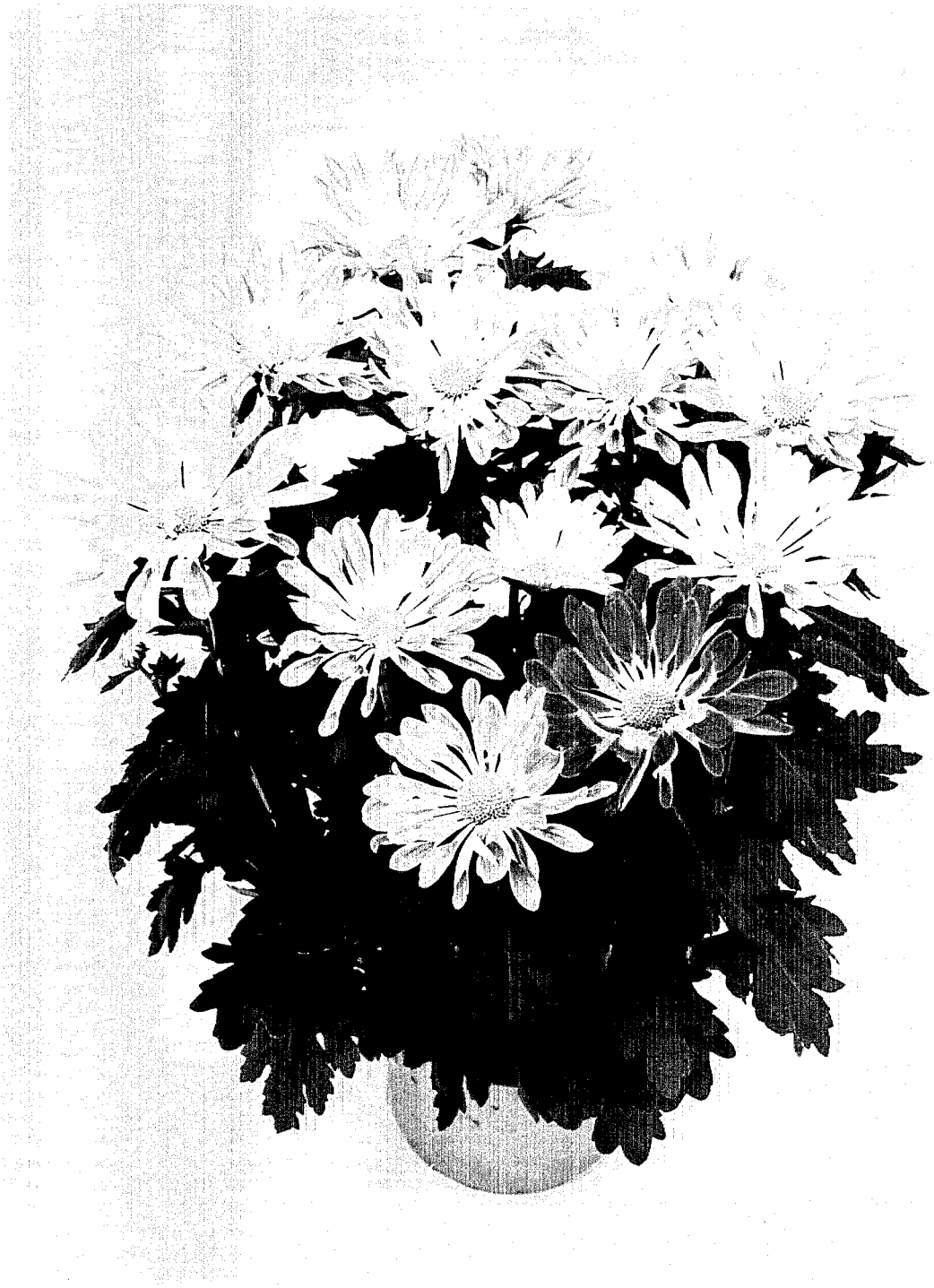

* * * * *